(12) United States Patent
Chim et al.

(10) Patent No.: US 6,415,186 B1
(45) Date of Patent: Jul. 2, 2002

(54) ACTIVE FEED FORWARD POWER CONTROL LOOP

(75) Inventors: Stanley Siu-Chor Chim, Valencia; Jason Chih-Shu Lee, Arcadia, both of CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/483,415

(22) Filed: Jan. 14, 2000

(51) Int. Cl.[7] ............................................... A61N 1/08
(52) U.S. Cl. ........................................ 607/57; 607/61
(58) Field of Search ....................... 607/27, 33, 55–57, 607/61; 128/903

(56) References Cited

U.S. PATENT DOCUMENTS

| | | | |
|---|---|---|---|
| 3,751,605 A | 8/1973 | Michelson | 179/107 |
| 4,400,590 A | 8/1983 | Michelson | 179/107 |
| 4,532,930 A | 8/1985 | Crosby et al. | 128/419 |
| 4,592,359 A | 6/1986 | Galbraith | 128/419 |
| 4,947,844 A | 8/1990 | McDermott | 128/421 |
| 5,411,537 A | * 5/1995 | Munshi et al. | |
| 5,702,431 A | 12/1997 | Wang et al. | 607/61 |
| 5,713,939 A | 2/1998 | Nedungadi et al. | 607/33 |
| 5,715,837 A | 2/1998 | Chen | 128/899 |
| 5,807,397 A | 9/1998 | Barreras | 607/61 |
| 5,824,022 A | 10/1998 | Zilberman et al. | 607/57 |
| 5,876,425 A | 3/1999 | Gord et al. | 607/56 |
| 5,891,183 A | 4/1999 | Zierhofer et al. | 607/57 |

* cited by examiner

Primary Examiner—Jeffrey R. Jastrzab
(74) Attorney, Agent, or Firm—Kenneth L. Green; Bryant R. Gold

(57) ABSTRACT

A feed forward power control loop is provided for a tissue stimulation system. The tissue stimulating system includes an external device and an implantable device. Only the amount of power required by the implantable device is transmitted across a transcutaneous transmission link to the implantable device from the external device, thereby reducing power fluctuations within the implantable device, and reducing the amount of power expended by the external device. In one embodiment, the power control loop is used with a cochlear stimulating system that includes an externally wearable signal receiver and processor (WP) and an implanted cochlear stimulator (ICS). The feed forward power control loop predicts the power requirements of the ICS. The prediction is used to determine the level of RF power to be transmitted by the WP. The transmitted RF power is received by the ICS and is stored in a "tank" capacitor that is used as a power source within the ICS for stimulating the cochlea and for powering the circuits within the ICS. The predictions of the ICS power requirements are based on a mathematical model and independent variables originating within the WP. The form of the mathematical model is based on a current model of the ICS. The coefficients of the mathematical model are obtained from the application of multiple regression analysis to a system of equations. The system of equations is derived from a plurality of measurements of the dependent and independent variables of the equation, recorded at different system operating points, and on the form of the mathematical model.

34 Claims, 6 Drawing Sheets

ACTIVE FEED FORWARD POWER CONTROL LOOP

BACKGROUND OF THE INVENTION

The present invention relates to the efficient utilization of power in body tissue stimulators, and more particularly to an improved power control loop for implantable cochlear stimulator systems. Such implantable cochlear stimulator systems provide improved hearing for the hearing impaired. The power control loop serves the important function of providing power to the implanted part of the cochlear stimulator system and the efficiency of the power control loop is critical in developing the miniaturized systems of the future.

U.S. Pat. No. 4,400,590 issued Aug. 23, 1983 for "Apparatus for Multi-Channel Cochlear Implant Hearing Aid System" describes and illustrates a system for electrically stimulating predetermined locations of the auditory nerve within the cochlea of the ear, which system includes a multi-channel intra-cochlear electrode array. The electrode array comprises a plurality of exposed electrode pairs spaced along and embedded in a resilient curved base for implantation in accordance with the method of surgical implantation described in U.S. Pat. No. 3,751,605 issued Aug. 7, 1973 for "Method of Inducing Hearing." The hearing aid system described in the '590 patent receives audio signals at a signal processor located outside the body of a hearing impaired patient. The processor converts the audio signals into analog data signals which are transmitted by a cable connection through the patient's skin to the implantable multi-channel intra-cochlear electrode array. The analog signals are applied to selected ones of the plurality of exposed electrode pairs included in the intra-cochlear electrode array to electrically stimulate predetermined locations of the auditory nerve within the cochlea of the ear where the intra-cochlear electrode array is positioned.

The cochlea stimulating system described in the '590 patent is limited in the number of channels of information, the speed of transfer of stimulating signals to the cochlea and the fidelity of the signals. Also, the cable connection through the skin of the patient to the intra-cochlear electrode array is undesired in that it interferes with the freedom of movement of the patient and represents a possible source of infection.

U.S. Pat. No. 4,532,930, issued Aug. 6, 1985 for "Cochlear Implant System For an Auditory Prosthesis" describes and illustrates a multiple electrode system which does not employ a through the skin connector. While multiple electrodes are employed to stimulate hearing, the system only operates with a single pulsatile output stimulating a single electrode channel at any given time. Such a sequential system is limited in speed of operation, and does not provide for analog operation where continuous stimulating signals, controllable in amplitude, are simultaneously applied to a number of electrode channels. Further, the system is subject to charge imbalance with misprogramming or circuit fault and inefficient use of electrical power. Moreover, once the stimulator unit is implanted there are no means for monitoring its ongoing circuit operation or power requirements so as to optimize its continued operation.

U.S. Pat. No. 4,592,359, issued Jun. 3, 1986 for "Multi-Channel Implantable Neural Stimulator" describes a cochlear implant system having 4 current sources and 4 current sinks per channel, controlled by series switches, to provide 16 different circuits for supplying 16 levels of 2 polarities to each output channel. In a pulsatile mode, the system provides for simultaneous update (amplitude control) and output to all channels. However, the system does not permit simultaneous analog update and output on all channels and the electrode pairs for each channel are not electrically isolated from all other electrode pairs whereby undesired current leakage may occur. Further, once the stimulator is implanted there are no means for monitoring its ongoing circuit operation or power requirements so as to optimize its continued operation.

U.S. Pat. No. 4,947,844, issued Aug. 14, 1990 for "Receiver/Stimulator For Hearing Prosthesis" describes and illustrates a multiple channel electrode system. The system includes an implantable receiver/stimulator connected to an implantable electrode array. Included in the implantable receiver/stimulator is a transmitter for telemetering one electrode voltage, measured during stimulation, to an external receiver for monitoring and analysis as an indicator of proper operation of the implantable stimulator. The transmitter comprises an oscillator operating at a frequency of about 1 MHz. The output of the oscillator is coupled to the implant's receiving coil. The oscillator signal, when received after transmission, is demodulated to recover the selected voltage waveforms. Unfortunately, such a telemetry system is not only limited to the monitoring of one voltage, but the simultaneous transmission of the telemetry signal and reception of the input carrier signal results in undesired modulation and possible loss of input data.

For cochlear stimulator applications, it is generally desirable to employ a cochlear stimulator that is driven by a behind-the-ear speech processor, e.g., of the type described in U.S. Pat. No. 5,824,022 issued Oct. 20, 1998 for 'Cochlear stimulation system employing behind-the-ear speech processor with remote control.' Behind-the-ear speech processors offer several advantages, but because of their small size are limited in the size of the battery they may carry (which in turn limits the useful life of the battery.) The small battery size results in a requirement for very low power dissipation. Although low power digital electronics have enabled digital hearing aids, this technology is only part of the answer for implantable stimulators. This is because an implantable stimulator, e.g., a cochlear stimulator, requires additional variable current to stimulate the target tissue, e.g., the auditory nerve within the cochlea, and this power must be transferred across a transcutaneous link, that is, at best, only about 50% efficient. While digital hearing aids only need to drive a transducer that uses less than one milliwatt (mW) of power, an implantable tissue stimulator may require up to 50 mW of stimulus power, which means (assuming a 50% transcutaneous link transfer efficiency) the need to transmit up to 100 mW of power to the implant device. Since power is proportional to the square of the voltage, it would thus be desirable to have a way to precisely and actively control the voltage in the implant device to track the output power requirements of the device. For example, for a cochlear stimulator, where room sound and speech levels are variant, it would be desirable to track speech and system variations and make automatic adjustments in the input power that track these variations, thereby only transmitting power to the implant device that is needed for the current conditions, thereby increasing the life of the battery.

U.S. Pat. No. 5,876,425, issued Mar. 2, 1999 for "Power Control Loop for Implantable Tissue Stimulator" describes a feedback power control loop utilizing back telemetry from the implantable device. The Implantable Cochlea Stimulator (ICS) utilizes a tank capacitor as an internal rechargable power source. The ICS monitors the voltage level of the tank capacitor and back transmits the tank capacitor voltage to the Wearable Signal Receiver and Processor (WP). Based on the back transmitted tank capacitor voltage, the WP computes the power level to be transmitted to the ICS to maintain the tank capacitor voltage within acceptable levels. While the approach taught in the '425 patent provides advantages over previous approaches that transmit power based on the peak ICS power requirement, it also results in delays in the calculation of the power requirements. The delays in the response of the power control loop result in too much power being transmitted at times, and this power is dissipated versus being stored. The requirement to continuously monitor the tank capacitor voltage requires that the implantable device expend power to digitize the measurement, and additional power is required to back transmit the tank capacitor voltage measurements. The power dissipation resulting from excessive power transmission and the power required to continuously provide tank capacitor voltage measurements, result in a requirement for either a larger battery in the WP, or more frequent recharging. The desire to develop a cochlear stimulator that is driven by a behind-the-ear speech processor further motivates the development of more efficient power control.

Accordingly, there is a continuing need for greater efficiency in supplying power to the implantable stimulator unit of the system to optimize system operation and power efficiency. The present invention satisfies such needs.

SUMMARY OF THE INVENTION

The present invention addresses the above and other needs by providing an active feed forward Power Control Loop (PCL) for implantable devices. Many implantable devices, and Implantable Cochlea Stimulator (ICS) systems in particular, require power to be supplied transcutaneously from an external device to an implantable device. A power supply method utilizing the wireless transmission of power from the external device to the implantable device is preferred over methods requiring a cable connection through the skin of the patient to the implantable device, because through the skin cables interfere with the freedom of movement of the patient and represents a possible source of infection. The use of a wireless power transmission from the external device to the internal device results in a requirement to control the amount of power transmitted by the external device.

Power for short term use is typically stored within the implantable device in a power storage device, for example, a tank capacitor. The tank capacitor is charged by RF power transmitted transcutaneously from the external device. The power source within the external device is generally a rechargeable battery. The size of the battery and the frequency of recharging is determined by the efficiency of the power use within the system. Due to the nature of the power storage within the implantable device, any power transmitted to the implantable device, in excess of that required to maintain the charge of the tank capacitor, is dissipated. As a result, optimal power utilization within the system requires that the power transmitted to the implantable device be a function of the instantaneous tank capacitor voltage.

The present invention advantageously utilizes a feed forward PCL, with a model of tank capacitor voltage as a function of the input speech level and the transmitted power level. A model of tank capacitor voltage is developed based on the implantable device circuitry, and as a function of externally measurable or controllable parameters. However, due to variable physical characteristics of the patient and the electronics (e.g. the RF power transmission efficiency or the impedance between electrodes,) the tank voltage model contains several unknown coefficients. The coefficients of the model are determined by operating the ICS system at various operating points for all of the independent parameters that drive the tank capacitor voltage. The values of all of the parameters and the resulting tank capacitor voltage are recorded during the patient fitting process as a set for each operating point. The total number of operating points is preferably several times the number of independent parameters. The results of the data collection are used as inputs to a multiple regression analysis. The multiple regression analysis results in a set of coefficients for the model of the tank capacitor voltage. During subsequent system operation, the tank capacitor voltage is estimated based on the model, and power is provided to the implantable device to maintain the desired tank capacitor voltage. Should the model drift with time, it may be periodically updated by back telemetry of the actual tank capacitor voltage.

In accordance with one aspect of the present invention, there is provided a timely estimate of the power requirements of the implantable device which results in a faster response to changes in the power requirements. By anticipating changes in the power requirements, the feed forward PCL reduces voltage downswings and subsequent voltage overshoot and thus provides a more efficient power utilization. The efficient use of the external device's power permits the battery in the external device to be made as small and light as possible which is advantageous for the development of improved behind-the-ear speech processors.

It is an additional feature of the present invention to eliminate the requirement for continuous measurement of the tank capacitor voltage within the implantable device, and continuous back telemetry of the tank capacitor voltage from the implantable device to the external device. The requirement to continuously monitor the tank capacitor voltage requires that the implantable device expend power to digitize the measurement, and additional power is required to back transmit the tank capacitor voltage measurements. By avoiding most or all of the requirement to provide tank capacitor voltage to the WP, the power required by these two steps is avoided.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
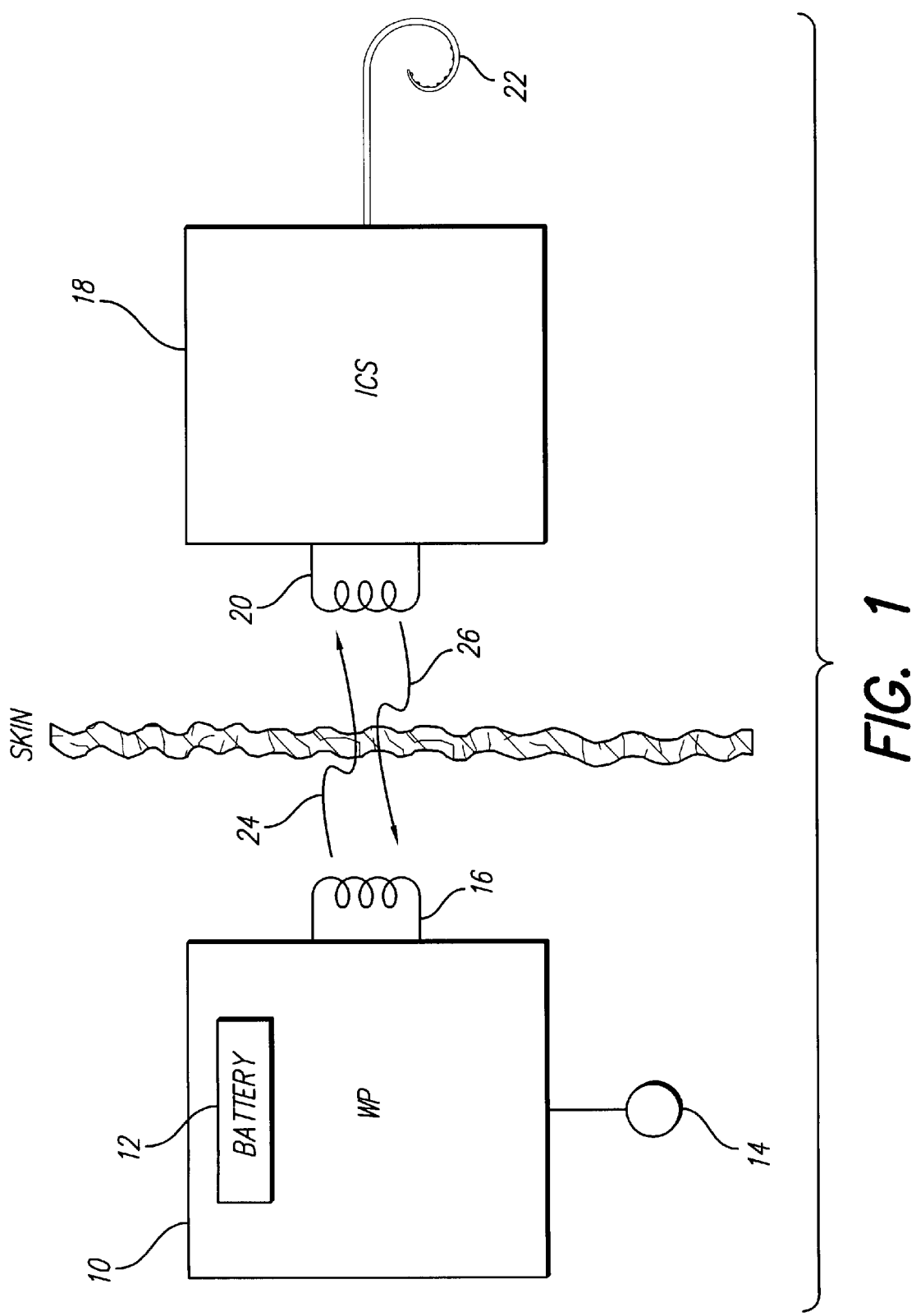
FIG. 1 depicts a diagram of a cochlea stimulating system.

The active feed forward Power Control Loop (PCL) of the present invention computes the required power level for the wireless transmission of power from an external device to an implantable device in a body tissue stimulation system. More particularly, as shown in FIG. 1, the present invention applies to the RF power transmission from an Externally Wearable Signal Receiver and Processor (WP) 10 to an Implantable Cochlear Stimulator (ICS) 18 of a cochlear stimulation system. The invention is particularly useful where the entire WP 10 is meant to be worn behind-the-ear, and where, due to battery size and weight limitation, the power requirements of such behind-the-ear WP needs to be minimized. It is to be understood, however, that even though the preferred embodiment described herein relates to a cochlear stimulation system, the invention need not be limited to a cochlear stimulation system. Rather, any implantable stimulator that derives its operating power from an external device, particularly an external device that is powered from a battery or other limited power source, may benefit from the present invention.

As seen in FIG. 1, the Externally Wearable Signal Receiver and Processor (WP) 10, and the Implantable Cochlear Stimulator (ICS) 18 are the main elements of the cochlear stimulation system. A microphone 14 is connected to the WP 10. The microphone 14 converts acoustic energy into electrical energy and provides the electrical energy as an input signal to the WP 10. The WP 10 processes the signal and transmits the result to the ICS 18 through a forward telemetry link 24 using the WP coil 16. The ICS 18 receives the signal through an ICS coil 20. The WP coil 16 may be functionally considered as a transmitting antenna, and the ICS coil 20 may similarly be considered as a receiving antenna. In operation, such two coils 16 and 20 are typically inductively coupled to each other. The ICS 18 further processes the signal and provides current to the electrode array 22 to provide nerve stimulation.

The WP 10 also includes a battery 12 as the WP's power source. The battery 12 also provides power to the ICS 18 through the forward telemetry link 24, also using the WP coil 16 to as the transmitting antenna. The ICS receives the transmitted power using the ICS coil 20 as the receiving antenna.

In addition to receiving power through the forward telemetry link 24, the ICS 18 also provides status information to the WP 10 through a back telemetry link 26. The ICS transmits the status information via the back telemetry link 26 using the ICS coil 20 as a transmitting antenna, and the WP 10 receives the status information using the WP coil 16 as a receiving antenna.

Figure 2:
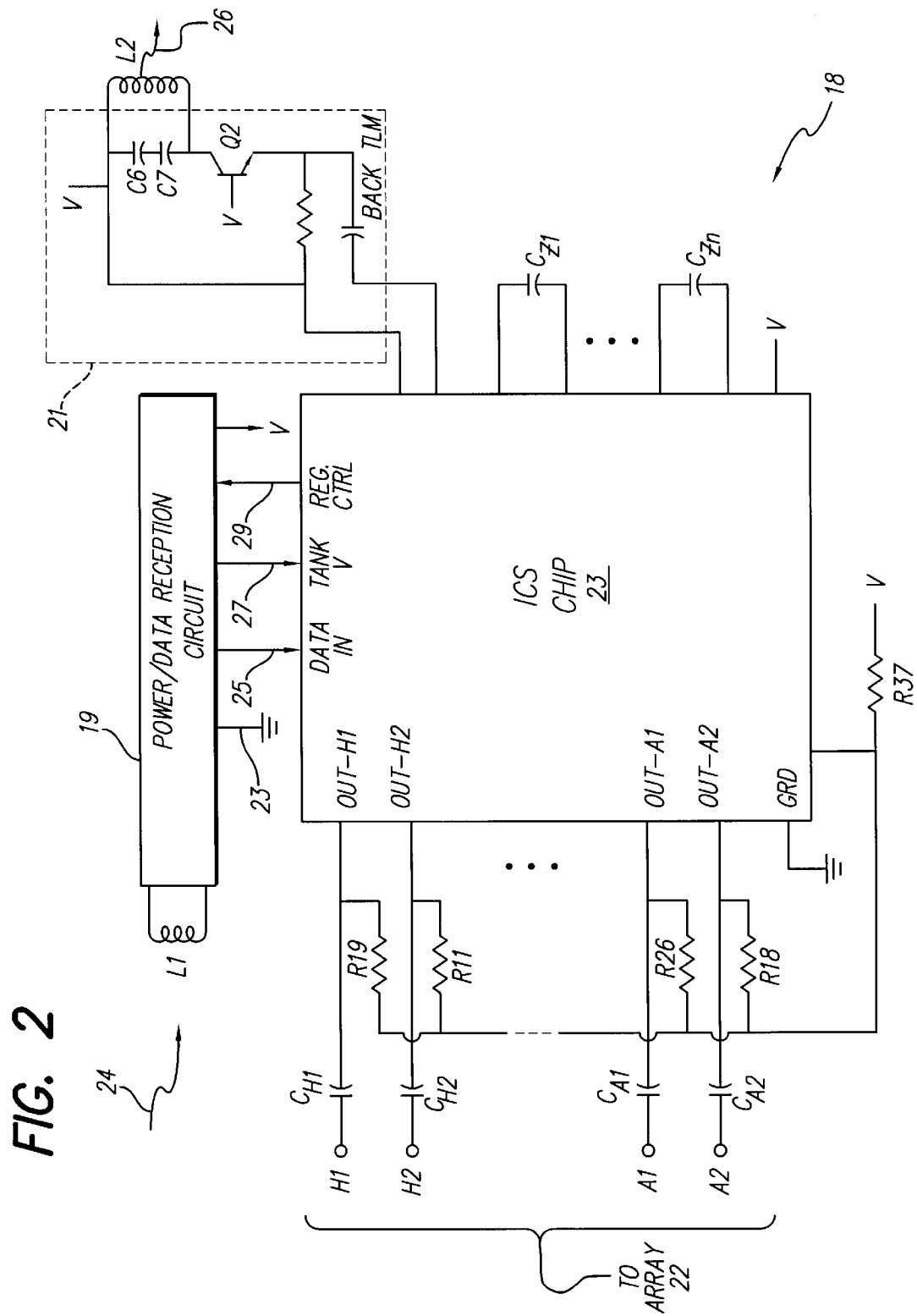
FIG. 2 shows a simplified diagram of an implantable cochlear system (ICS)

Turning next to FIG. 2, a simplified schematic diagram of an exemplary ICS 18 is shown. The circuitry shown in FIG. 2 is "simplified" in that not all of the components used in the ICS 18 are shown; but sufficient components are shown to clearly teach the circuit configuration employed within the ICS 18 that is relevant to the present invention.

As seen in FIG. 2, the ICS 18 includes a receiving coil L1 connected to Power/Data Reception Circuit 19. The Power/Data reception circuit 19 receives at least two inputs. A first input is the forward telemetry signal 24 received by the coil L1. A second input is a control signal, on signal line 29, which is used within the Power/Data reception circuit 19 to control the tank voltage. The Power/Data reception circuit 19 also provides at least three outputs. A first output is a voltage V which, in reference to a ground reference terminal 23, provides the operating power for the ICS 18. A second output, on signal line 25, is data that is received through the receiving coil L1. A third output, on signal line 27, provides a monitoring point through which the tank voltage may be measured.

As further seen in FIG. 2, a transmission coil L2 is also included as part of the ICS 18. This coil L2 is connected to back telemetry circuit 21. The back telemetry circuit 21 includes a transistor switch Q2 which turns the coil L2 on and off to control an LC-circuit made up of coil L2 and capacitors C6 and C7 in accordance with the data that is to be transmitted from the coil L2. The back telemetry circuit 21 thus provides a means for sending back telemetry signals 26 to the external WP 10 (FIG. 1).

The Power/Data reception circuit 19 and back telemetry circuit 21 are connected to an ICS Chip 23. The ICS Chip 23 may actually comprise more than one integrated circuit chip, but only one chip is shown in FIG. 2 for simplicity. The ICS chip 23 includes all of the data signal processing (DSP) circuitry and analog driver circuitry necessary to receive data and power from the Power/Data reception circuitry 19 and to generate appropriate stimulation current pulses that are delivered to the electrode array 22 through at least two electrode terminals of a multiplicity of such terminals which are connected to the electrode array 22 (FIG. 1).

The electrode terminals are illustrated in FIG. 2 as terminals A1, A2, B1, B2, . . . H1, H2. (Only the A1, A2 and H1, H2 terminals are shown in FIG. 2, but it is to be understood that the other terminals are the same as those shown.) Sensing resistors R26 and R18 are coupled to the electrode terminals A1 and A2, respectively, and similar sensing resistors R19 and R11 are connected to electrode terminals H1 and H2, respectively. It is through these sensing resistors that the amount of current flowing to or from a given electrode terminal may be monitored. Each electrode terminal is connected to the ICS chip 23 through a respective coupling capacitor. That is, electrode terminal A1 connects to the ICS chip 23 through coupling capacitor $C_{A1}$, electrode terminal A2 connects to the ICS chip 23 through coupling capacitor $C_{A2}$, and so on, with electrode terminal H1 connecting to the ICS chip 23 through coupling capacitor $C_{H1}$, and electrode terminal H2 connecting to the ICS chip 23 through coupling capacitor $C_{H2}$. Various other capacitors $C_{Z1}$ through $C_{Zn}$, external to the ICS chip 23, are also used as part of the ICS circuitry. In particular, each of these capacitors may be used to assist each of the driver circuits (part of the ICS chip circuitry 23) that are connected to the electrode terminals A1, A2, . . . H1 and H2. The driver circuits connected to each electrode terminal may be of the type taught in U.S. Pat. No. 6,181,969 issued Jan. 30, 2001 for "Programmable current output stimulus stage for implantable device", which patent is assigned to the same assignee as is the present application, and which application is incorporated herein by reference.

Figure 3:
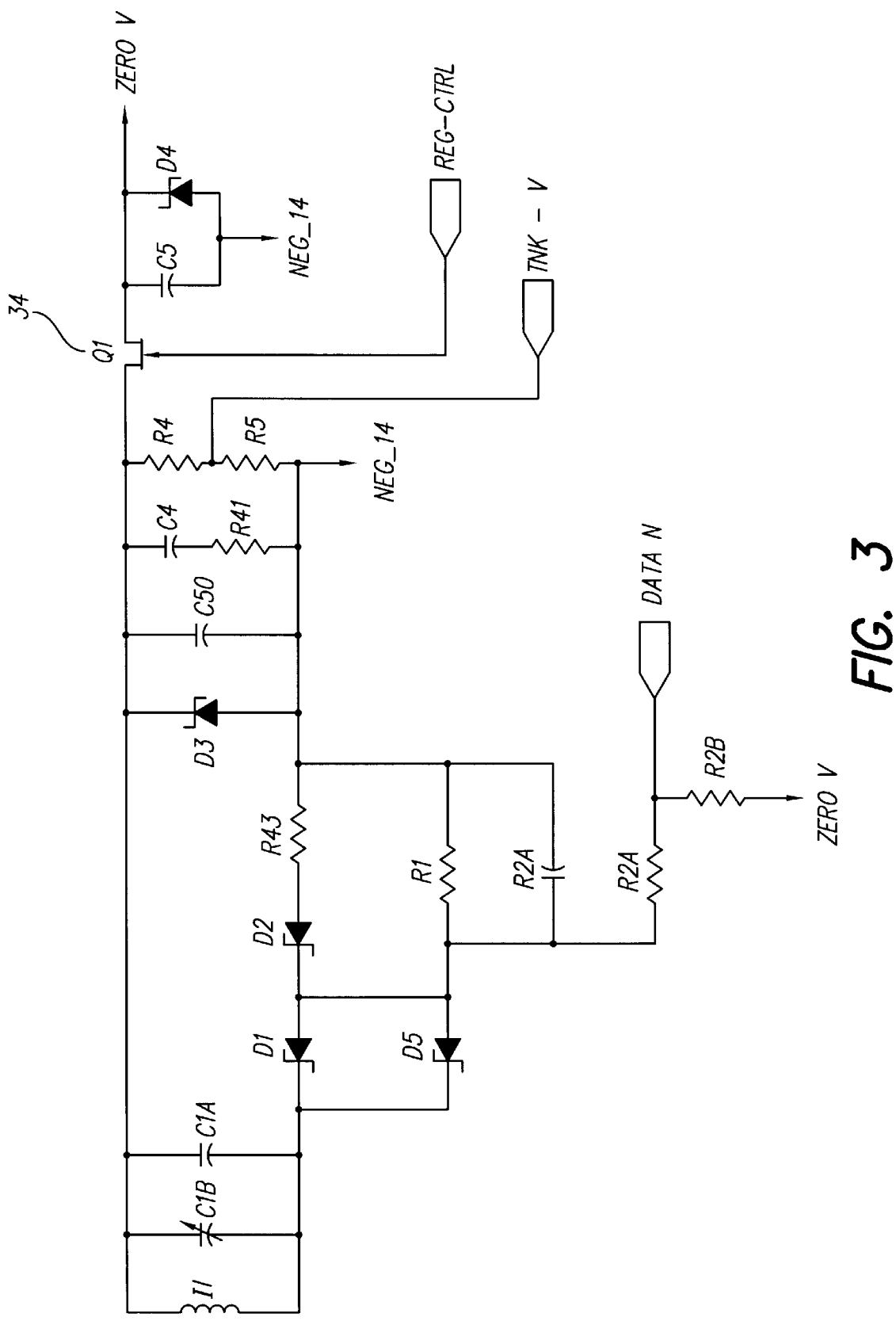
FIG. 3 shows the Power/Data Reception circuit of FIG. 2.

Turning next to FIG. 3, a schematic diagram of a preferred embodiment of the Power/Data reception circuit 19 is shown. The ICS 18 requires power both for signal (data) processing within the ICS 18, and for nerve stimulation by the electrode array 22. The ICS 18 power requirements are met by capacitors C4 (hereafter also referred to as the tank capacitor) and C5. Capacitor C5 supplies instantaneous power to the ICS. Whenever the voltage across capacitor C5 drops below 14 volts, a JFET transistor 34 automatically turns on to close the circuit comprising capacitor C5 and the tank capacitor C4, thus recharging capacitor C5 from tank capacitor C4. The tank capacitor C4 is designated as the tank capacitor because it provides a reservoir of power for capacitor C5. If the tank capacitor C4 fails to adequately recharge the capacitor C5, and the voltage across capacitor C5 drops below 11 volts, the system shuts down. Therefore, it is essential for system operation that the WP 10 provides sufficient power to the ICS 18 to adequately charge the tank capacitor C4. The voltage across the tank capacitor C4 is designated as the tank voltage (hereafter $V_{tank}$). The goal of the RF power transmission is to maintain $V_{tank}$, in a range suitable for charging the capacitor C5. The selection of a target value for $V_{tank}$ is based on upon the fluctuations in $V_{tank}$, observed during the process of fitting the cochlear stimulation system to the patient. The target voltage is preferably between 14 and 15 volts. For a patient exhibiting very large swings in $V_{tank}$, the target voltage is set high, and for a patient exhibiting small swings in $V_{tank}$, the target voltage is set low.

Whenever excess power is transmitted to the implantable device, that power is eventually dissipated and not stored, thereby reducing the life of the power source within the WP 10. Such inefficient use of power results in a requirement for a larger battery, or more frequent replacement or recharging of the battery of the WP 10. Allowing for a small battery size is important in any WP 10, and is essential in a behind-the-ear WP 10 where weight and space are extremely limited. As described herein, the present invention provides a means to estimate $V_{tank}$, so that the WP 10 can automatically adjust the power the WP 10 provides to the ICS 18 to maintain $V_{tank}$ near the target voltage. In this manner, only the power needed by the ICS 18 at any given time is transmitted to the ICS 18 from the WP 10. Thus, the present invention advantageously avoids inefficient use of power and therefore contributes to minimizing battery size and/or increases battery life.

When insufficient power is transmitted to the implantable device, $V_{tank}$ may drop excessively. If the tank capacitor C4 is unable to adequately re-charge the capacitor C5, and the voltage on capacitor C5 drops below 11 volts, the systems shuts down. Thus, by reducing time lags in the power control loop and better maintaining $V_{tank}$, the present invention reduces the likelihood of such shutdowns.

As previously described, U.S. Pat. No. 5,876,425, issued Mar. 2, 1999 for "Power Control Loop for Implantable Tissue Stimulator" describes a feedback power control loop utilizing back telemetry from the implantable device. The ICS disclosed in the '425 patent monitors the voltage level of the tank capacitor C4 and back transmits the tank capacitor voltage to the WP. The WP then computes how much power must be transmitted to the ICS to maintain the tank capacitor voltage within acceptable levels. While this approach provides advantages over previous approaches, it also results in delays in the calculation of the RF power requirements. The delays in the response of the power control loop result in large swings in tank capacitor voltage. Too much power is transmitted at times, which power is dissipated versus being stored, and too little power is transmitted at other times, resulting in low tank capacitor voltage, which low voltage may result in system shut down. The approach described in the '425 patent also results in inefficient use of processing capability of ICS 18 in that it must continuously monitor and transmit $V_{tank}$ from the ICS to the WP. The present invention advantageously replaces the feedback feature of the '425 patent, by providing a model of the ICS power requirement in the WP 10. In other material aspects, the present invention is similar to the cochlea stimulation system described in the 425 patent. The '425 patent is incorporated herein by reference.

Figure 4:
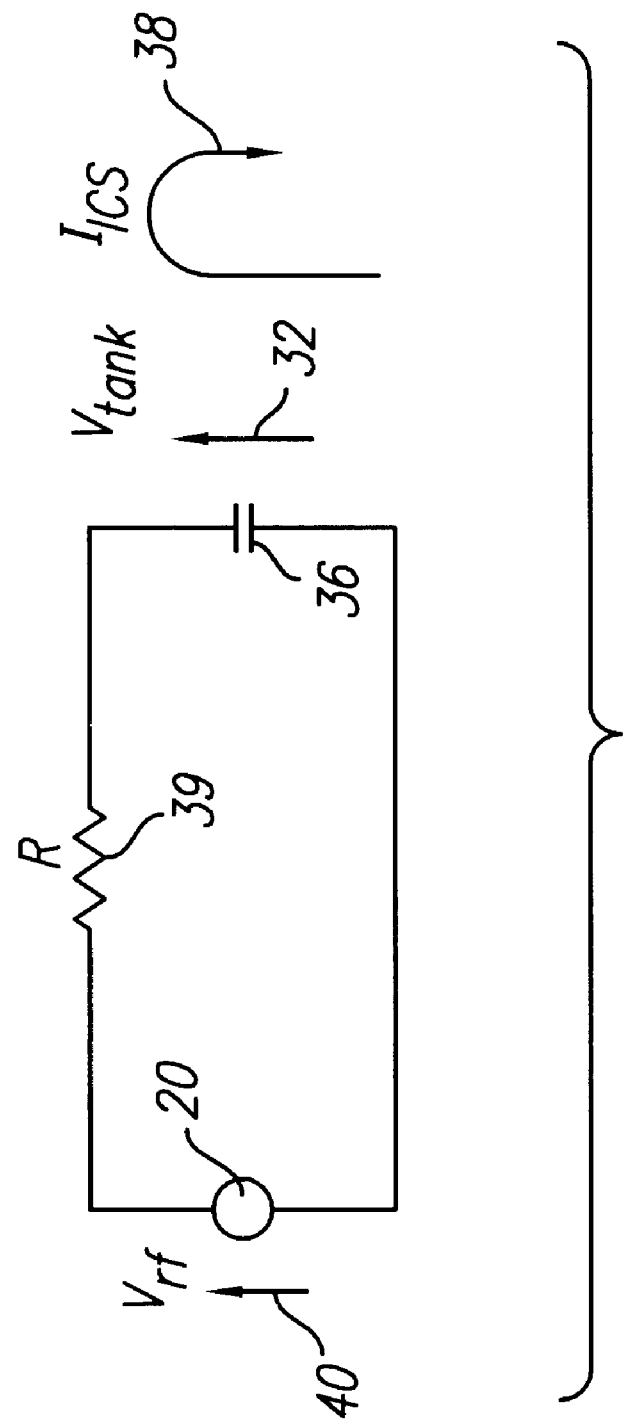
FIG. 4 depicts an ICS current model.

Turning next to FIG. 4, an ICS current model for a preferred embodiment of the invention is illustrated. In the model shown, the RF voltage 40 charges the ICS capacitance 36, and the ICS current 38 discharges the ICS capacitance 36. The voltage across the ICS capacitance 36 is $V_{tank}$. The resulting equation for the ICS current is:

$$C^{*}(\Delta V_{tank})/(\Delta t)=1/(2r)^{*}(V_{rf}-V_{tank})-(I_{ICS}) \tag{1}$$

where:

C is the ICS capacitance 36;

$V_{tank}$ is tank voltage developed across capacitance 36;

t is time;

r is a resistance 39, present between the RF voltage source 40 and the ICS capacitance 36;

$V_{rf}$ is the RF voltage 40 received by the ICS 18 through forward telemetry link 24 (see FIG. 1); and $I_{ICS}$ is the current being drawn by the ICS 18 for data and signal processing and to the electrode array 22 for tissue stimulation.

The current model shown FIG. 4 is based on the power and data reception circuit shown in FIG. 3. A variety of circuits may be designed for power and data reception in an implantable device, and, appropriate current models may be derived for these various embodiments. Such various embodiments, and therein resulting current models, will be apparent to those skilled in the art, and fall within the scope of the present invention.

The ICS circuit model shown in FIG. 4 has a very short settling time (i.e., a very small time is required for $V_{tank}$ to reach a new steady state voltage after inputs change) compared to the feed forward PCL loop update rate. As a result the left side of equation (1) becomes zero very quickly, and the ICS current equation (1) may be evaluated at steady state. This results in:

$$V_{tank}=V_{rf}-2r^{*}I_{ICS} \tag{2}$$

Assuming that the ICS current, $I_{ICS}$, is the sum of the current required for tissue stimulation, $I_{stim}$, and the quiescent current required for data and signal processing within the ICS, $I_q$, equation (2) becomes:

$$V_{tank}=-2^{*}r^{*}I_q-2^{*}r^{*}I_{stim}+V_{rf} \tag{3}$$

The actual RF voltage ($V_{rf}$) received by the ICS 18 varies and is not directly available to the WP 10, but $V_{rf}$ may be assumed to be proportional to the transmitted RF power level ($P_{rf}$). Additionally, the stimulation current, $I_{stim}$, may be assumed to be a quadratic function of the input speech level (dBSPL) in dB. Both RF power level, and dBSPL are available within the WP 10. Applying these assumptions equation (3) becomes:

$$V_{tank}=b_0+b_1(\text{dB}SPL-c_1)+b_2((\text{dB}SPL-c_1)^2+b_3(P_{rf}+c_2) \tag{4}$$

where:

dBSPL is the measured input speech level in dB;

$P_{rf}$ is the RF power level;

$b_0$, $b_1$, $b_2$, and $b_3$ are unknown coefficients;

$c_1$ is 67.5 minus the patient's input dynamic range (IDR), and is unique for each embodiment of patient, hardware, and software; and $c_2$ is an offset specific to the hardware implementation.

It is assumed that the measurements of $V_{tank}$, dBSPL, and $P_{rf}$, are corrupted by noise and by random and quantization errors in the measurement of $V_{tank}$. Therefore, coefficients, $b_0$, $b_1$, $b_2$, and $b_3$, are best determined for the particular patient and hardware, by applying multiple regression analysis.

The first step in obtaining the coefficients is to collect the necessary measurements. The measurements are obtained during the patient fitting process following the implanting of the ICS. The procedure is summarized as follows:

1. Stimulate the patient with speech noise;
2. Record the noise level (dBSPL);
3. Record the RF power level (ranges from 0 to 15);
4. Record $V_{tank}$;
5. Repeat steps 1 through 4 at different speech noise levels (preferably nine levels spaced between 63 and 103);
6. Repeat steps 1 through 5 at different RF power levels (preferably six levels from 1 to 6);
7. Record the patient's input dynamic range (IDR).

After collecting the necessary measurements, compute $c_1$ from the measured IDR:

$$c_1 = 67.5 - IDR. \quad (5)$$

Set $c_2$ based on the hardware configuration:

$$c_2 = 16. \quad (6)$$

The results of the above data collection are used to form a system of equations:

$$V\text{tank}(1) = b_0 \ast X(1,1) + b_1 \ast X(1,2) + b_2 \ast X(1,3) + b_3 \ast X(1,4)$$

$$V\text{tank}(2) = b_0 \ast X(2,1) + b_1 \ast X(2,2) + b_2 \ast X_1(2,3) + b_3 \ast X(2,4)$$

$$V\text{tank}(3) = b_0 \ast X(3,1) + b_1 \ast X(3,2) + b_2 \ast X_1(3,3) + b_3 \ast X(3,4) \quad (7)$$

$$\ldots$$

$$V\text{tank}(n) = b_0 \ast X(n,1) + b_1 \ast X(n,2) + b_2 \ast X(n,3) + b_3 \ast X(n,4)$$

where:
 $X(n,1) = 1$;
 $X(n,2) = dBSPL(n) - c_1$;
 $X(n,3) = (dBSPL(n) - c_1)^2$;
 $X(n,4) = P_{rf}(n) + c_2$ The system of equations (7) may be rewritten in matrix form as:

$$\overline{V_{\text{tank}}} = \overline{X} \ast \overline{B} \quad (8)$$

where:
 $V_{tank}$ is a n×1 column vector of $V_{tank}$ measurements;
 X is an n by 4 vector of functions of measurements defined above;
 B is a 4×1 vector of coefficients $[b_0\ b_1\ b_2\ b_3]$.

A minimum squared error solution for this system of equations (7) is obtained by finding the minimum of the error function J(X) with respect to the measurements $V_{tank}$ and X, where J(X) is:

$$J(X) = [\overline{V_{tank}} - \overline{X} \ast \overline{B}]^T [\overline{V_{tank}} - \overline{X} \ast \overline{B}] \quad (9)$$

where:
 $[\overline{V_{tank}} - \overline{X} \ast \overline{B}]^T$ is the transpose of the matrix $[\overline{V_{tank}} - \overline{X} \ast \overline{B}]$.

Differentiating J(X) with respect to X and setting the result equal to zero yields the result:

$$(X^T X) B = X^T V_{tank} \quad (10)$$

The coefficients, B, are solved for:

$$B = (X^T X)^{-1} X^T V_{tank} \quad (11)$$

By way of example, data was collected for a patient and is provided in Table 1. Measurements of $V_{tank}$ are in the first column of Table 1 (i.e., $V_{tank}(n) = data(n,1)$). The second column of Table 1 is $P_{rf}$ the PF power level, and the third column is dBSPL, the measured input speech power level. Based on the definition of parameters following equation (7), the X matrix is computed from the second and third columns of the data matrix:

$X(n,1) = 1$;
$X(n,2) = data(n,3) - c_1$;
$X(n,3) = (data(n,3) - c_1)^2$;
$X(n,4) = data(n,2) + c_2 \quad (12)$

TABLE 1 measured patient data

| $V_{tank}$ | $P_{rf}$ | dBSPL |
|---|---|---|
| 14.74 | 1 | 63 |
| 14.35 | 1 | 68 |
| 3.75 | 1 | 73 |
| 13.56 | 1 | 78 |
| 13.36 | 1 | 83 |
| 13.36 | 1 | 88 |
| 13.36 | 1 | 93 |
| 13.17 | 1 | 98 |
| 12.97 | 1 | 103 |
| 15.91 | 2 | 63 |
| 15.52 | 2 | 68 |
| 14.93 | 2 | 73 |
| 14.74 | 2 | 78 |
| 14.24 | 2 | 83 |
| 14.24 | 2 | 88 |
| 14.15 | 2 | 93 |
| 14.15 | 2 | 98 |
| 17.09 | 3 | 63 |
| 16.70 | 3 | 68 |
| 16.11 | 3 | 73 |
| 15.92 | 3 | 78 |
| 15.72 | 3 | 83 |
| 15.52 | 3 | 88 |
| 15.52 | 3 | 93 |
| 15.32 | 3 | 98 |
| 15.32 | 3 | 103 |
| 18.28 | 4 | 63 |
| 17.88 | 4 | 68 |
| 17.29 | 4 | 73 |
| 17.10 | 4 | 78 |
| 16.90 | 4 | 83 |
| 16.70 | 4 | 88 |
| 16.50 | 4 | 93 |
| 16.50 | 4 | 98 |
| 16.50 | 4 | 103 |
| 19.26 | 5 | 63 |
| 18.86 | 5 | 68 |
| 18.47 | 5 | 73 |
| 18.08 | 5 | 78 |
| 17.88 | 5 | 83 |
| 17.68 | 5 | 93 |
| 17.29 | 5 | 103 |
| 19.26 | 6 | 63 |
| 19.26 | 6 | 68 |
| 19.26 | 6 | 73 |
| 19.26 | 6 | 78 |

Applying multiple regression analysis (equation 11) to the data in Table 1 results in a coefficient vector:

$$B = [2.48\ -0.21\ 0.0013\ 1.14] \quad (13)$$

The result represented in Equation (13) was obtained using the regress function from the MATLAB© statistics toolbox. This particular function uses QR decomposition of X to reduce numerical sensitivity when X is poorly conditioned. Because of the likelihood of encountering poorly conditioned X matrices, and the matrix inversion required by multiple regression analysis, it may be necessary in some instances to apply a method of reducing numerical error. Those skilled in the art will recognize that other methods of reducing numerical sensitivity exist, and fall within the scope of the invention.

Figure 5A:
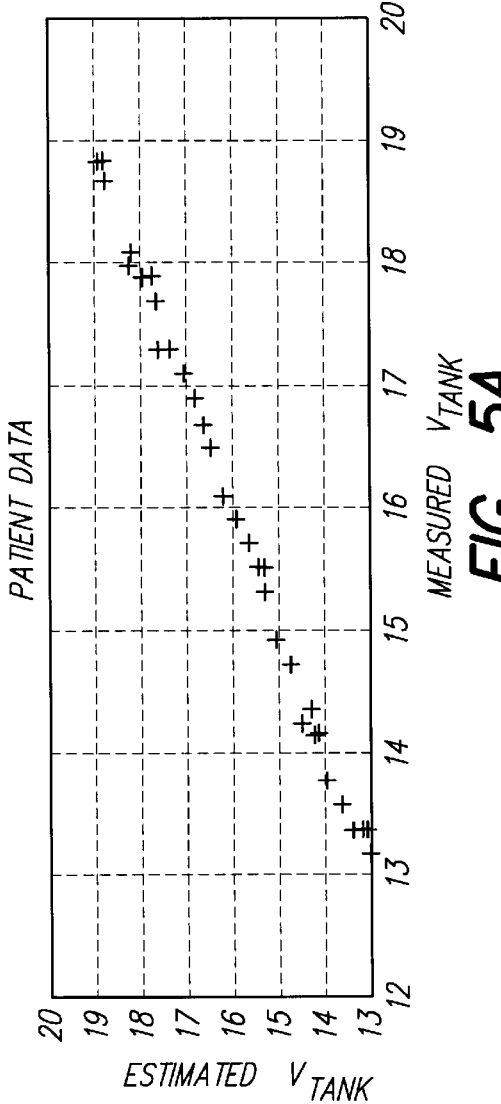
FIG. 5A depicts the measured tank capacitor voltage and the estimated tank capacitor voltage that resulted from the application of multiple regression analysis.
Figure 5C:
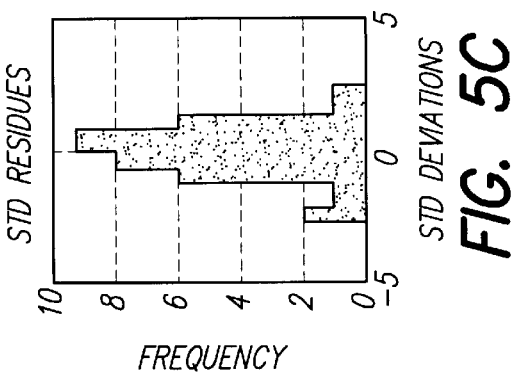
FIG. 5C depicts a histogram of the standard deviation of the estimation error.
Figure 5B:
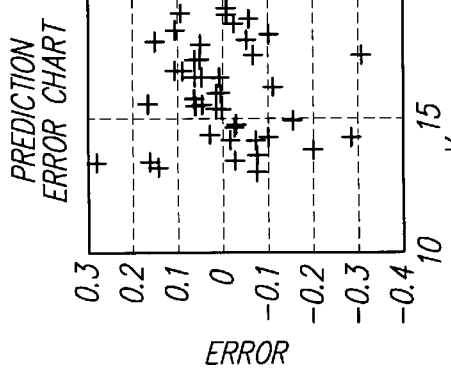
FIG. 5B depicts the tank capacitor voltage estimation error versus tank capacitor voltage.

Turning next to FIG. 5A, a plot of measured $V_{tank}$ versus estimated $V_{tank}$ using the coefficients in equation (13) is illustrated. FIG. 5B shows a plot of the prediction error from the same data. FIG. 5C presents a histogram of the standard deviations of the estimates. As can be seen from FIGS. 5A–5C, all of the estimates of $V_{tank}$ are within 0.3 volts of the measured value of $V_{tank}$. The small errors in the results presented in FIGS. 5A–5C show that the assumptions made in deriving equation (4) are valid.

In many instances, the coefficients, B, may be computed once during patient fitting and remain unchanged. However, if the hardware characteristics or the patient's impedance change sufficiently over time, a drift correction may be required. The original multiple regression need not be performed in real time, and may be performed on any computer using recorded data. Similarly, long term drift corrections may be based on data recorded in a physicians office, where computational requirements are not an issue. However, a short term drift correction capability implementable within the WP 10 requires that the calculations be done within the Digital Signal Processor (DSP) included within the WP 10. These calculations must be performed in addition to the calculations performed for speech processing, and include the inversion of a possibly poorly conditioned 4×4 matrix. Therefore, the method of correcting for short term drift must be simplified to fit within the processing resources. The method used by the present invention is to use back telemetry link 26 to periodically provide a measure of $V_{tank}$, measured within the ICS 18, to the WP 10. The preferred rate for providing $V_{tank}$ measurement is 2 Hz. The DSP within the WP 10 uses the measured $V_{tank}$ and the values of dBSPL and $P_{rf}$ available internally in the WP 10, to compute a corrected value for $b_0$ of equation (7):

$$b_0 = [Vtank(1) - b_1 * X(1,2) - b_2 * X(1,3) - b_3 * X(1,4)]/X(1,1) \quad (14)$$

where:
X(1,1)=1;
X(1,2)=dBSPL−$c_1$;
X(1,3)=(dBSPL−$c_1$)$^2$;
X(1,4)=$r_f$+$c_2$;
b1, b2, and b3 are the original coefficients computed by the multiple regression and are unchanged.

Figure 6:
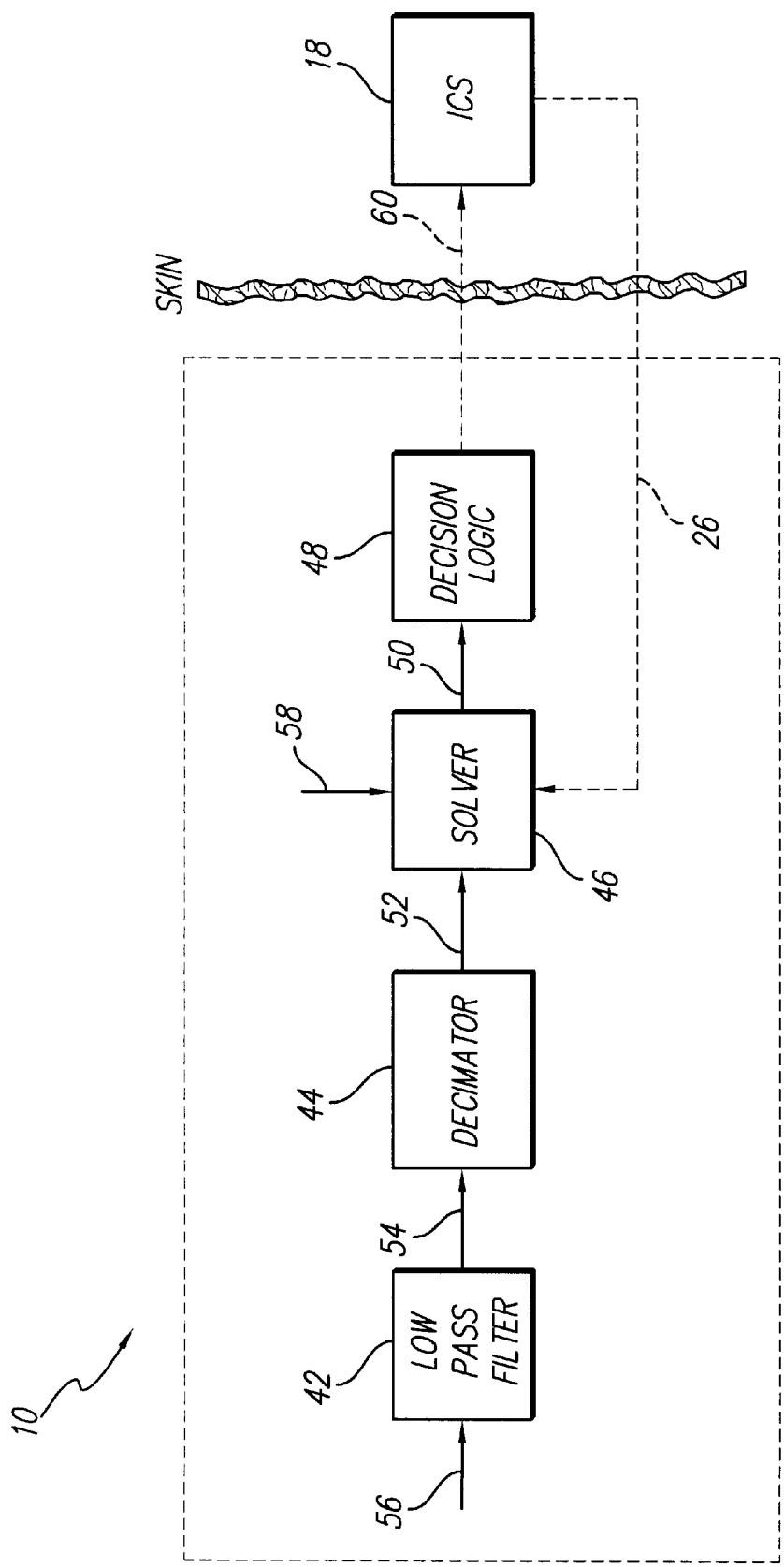
FIG. 6 depicts one implementation of the present invention.

A block diagram of one implementation of the present invention is provided in FIG. 6. The input signal power level, dBSPL, is computed within the WP 10 by digitizing the analog signal from the microphone 14 (FIG. 1) at a 17.4 kHz sample rate to create the digitized data 56. The digitized data 56 is then processed within the digital signal processor (DSP) circuitry of the WP 10. The functions carried out by such circuitry are illustrated in FIG. 6. The first step carried out by the DSP circuitry is to pass the digitized data through a low pass filter 42 in anticipation of decimation. Two bin averages are performed in cascade within the low pass filter 42 to generate the filtered data 54. The first average is taken over 20 samples. The second average is taken over 14 samples.

The next processing step is decimation 44 of the filtered data 54 by a factor of 10 (e.g., only every 10$^{th}$ sample is retained). This results in a sample rate 1.74 kHz. The result of such decimation is the signal identified in FIG. 6 as dBSPL 52.

The value of dBSPL 52 computed above is then used in the solver 46, along with the present RF power level($P_{rf}$) 58, and the coefficients resulting from the multiple regression analysis, to estimate $V_{tank}$, using equation (4). The estimate of $V_{tank}$ is then compared to a target $V_{tank}$, and a target RF power level 50 is computed based on the comparison. The target RF power level 50 is then used in decision logic 48 to compute the new RF power level 60 to be transmitted to the ICS 18.

As noted above, the same forward telemetry link 24 is used both to provide power to the ICS 18, and to provide data to the ICS. As a result there are limitations on how fast the RF power level can be increased or decreased without corrupting the signal component of the forward telemetry. Therefore, the time between changes in RF power is limited to a minimum time, preferably about 10 msec. The size of each change is also limited to a maximum value, preferably about 1/3 volt.

The measured value of $V_{tank}$ from the ICS 18 is periodically provided to the WP 10 through back telemetry link 26 (FIG. 1), preferably at a 2 Hz rate. Such value of $V_{tank}$ may then be used in the WP 10 to periodically correct for drift as described in equation (14) above. The processing required to correct for drift is preformed in the DSP circuits within the WP 10.

While the invention herein disclosed has been described by means of specific embodiments and applications thereof, numerous modifications and variations could be made thereto by those skilled in the art without departing from the scope of the invention set forth in the claims.

What is claimed is:

1. A feed forward power control loop for a body tissue stimulation system, comprising;
   an implantable device including circuitry and electrodes adapted to provide stimulation to body tissue; and
   an external device adapted to provide power to said implantable device, wherein said external device includes a mathematical model adapted to generate an estimate of the amount of power required by said implantable device, wherein the mathematical model does not require feedback from the implantable device to generate the estimate.

2. The feed forward power control loop of claim 1 wherein the mathematical model is based on an Implantable Cochlear Stimulation (ICS) system current model.

3. The feed forward power control loop of claim 1 wherein said mathematical model is adapted to generate an estimate of the amount of power required by said implantable device by multiplying coefficients by variables available within the external processor.

4. The feed forward power control loop of claim 3 wherein the coefficients are determined by a solution of a system of equations, wherein said system of equations is constructed using signal measurements taken while the body tissue stimulation system is in operation, and wherein said signal measurements include signal measurements originating in said external device.

5. The feed forward power control loop of claim 3 wherein the coefficients are determined by a solution of a system of equations, wherein said system of equations is constructed using signal measurements taken while the body tissue stimulation system is in operation, and wherein the signal measurements include signals measurements originating in said implantable device.

6. The feed forward power control loop of claim 3 wherein the coefficients are determined by a solution of a system of equations, wherein said system of equations is constructed using signal measurements taken while the body tissue stimulation system is in operation, and wherein said signal measurements comprise signal measurements taken for a particular patient and system combination.

7. The feed forward power control loop of claim 3 wherein the coefficients are determined by a solution of a system of equations, wherein said solution of a system of equations comprises a multiple regression analysis of said system of equations.

8. The feed forward power control loop of claim 1 wherein said mathematical model is an updatable mathematical model, wherein said updatable mathematical model comprises a mathematical model which may be updated during system operation.

9. The feed forward power control loop of claim 8 wherein said updatable mathematical model includes means for updating using new signal measurements, wherein said new signal measurements comprise signals that originate in at least one of the external device and the implantable device.

10. The feed forward power control loop of claim 9 wherein the updatable mathematical model is adapted to recalculate at least one of a plurality of coefficients of the updatable mathematical model based on the new signal measurements, wherein the remaining coefficients are held constant.

11. The feed forward power control loop of claim 1 wherein the implantable device comprises an Implantable Cochlea Stimulator (ICS).

12. The feed forward power control loop of claim 1 wherein the external device comprises a behind-the-ear processor.

13. The feed forward power control loop of claim 1 wherein said mathematical model comprises a mathematical representation of said circuitry and electrodes of the implantable device.

14. The feed forward power control loop of claim 13 wherein said mathematical representation of said circuitry and electrodes includes coefficients multiplied by variables available within the external processor.

15. The feed forward power control loop of claim 14 wherein the coefficients are determined by a solution of a system of equations, wherein said system of equations includes signal measurements taken while the body tissue stimulation system is in operation, and wherein said signal measurements include signal measurements originating in said external device.

16. The feed forward power control loop of claim 14 wherein the coefficients are determined by a solution of a system of equations, wherein said system of equations includes signal measurements taken while the body tissue stimulation system is in operation, and wherein the signal measurements include signal measurements originating in said implantable device.

17. The feed forward power control loop of claim 14 wherein the coefficients are determined by a solution of a system of equations, wherein said system of equations includes signal measurements taken while the body tissue stimulation system is in operation, and wherein said signal measurements comprise signal measurements taken for a particular patient and system combination.

18. The feed forward power control loop of claim 14 wherein the coefficients used by the mathematical representation of said circuitry and electrodes are determined by performing a multiple regression analysis of a system of equations.

19. The feed forward power control loop of claim 14 wherein said mathematical representation further comprises an updatable mathematical representation of said circuitry and electrodes which may be updated during system operation.

20. The feed forward power control loop of claim 19 wherein said updatable mathematical representation of said circuitry and electrodes is updatable based on new signal measurements, wherein said new signal measurements comprise signals that originate in at least one of the external device and the implantable device.

21. The feed forward power control loop of claim 20 wherein the updatable mathematical representation is updatable by recalculating at least one the coefficients of the updatable mathematical representation, based on the new signal measurements, wherein the remaining coefficients are unchanged.

22. The feed forward power control loop of claim 14 wherein the implantable device comprises an Implantable Cochlea Stimulator (ICS).

23. The feed forward power control loop of claim 14 wherein the external device comprises a behind-the-ear processor.

24. A tissue stimulating system comprising:
an implantable part including a power requirement
an external part including:
means for computing an estimate of the power requirement of the implantable part; and
means for providing power to the implantable part based on the estimate of the power requirement of the implantable part;
wherein the means for computing an estimate does not require feed-back from the implantable part.

25. The tissue stimulating system of claim 24 wherein the implantable device further includes a power storage device voltage, and wherein the power storage device voltage must be kept within a preferred range for efficient operation of the tissue stimulating system, and wherein the means for computing an estimate of the power requirement of the implantable device includes a model of the power storage device voltage.

26. The tissue stimulating system of claim 25 wherein the implantable device further includes a stimulation circuit, and wherein the model of the power storage device voltage comprises a mathematical model based on a current model of the stimulation circuit, wherein the mathematical model includes coefficients which are determined by a solution of a system of equations using a multiple regression analysis, wherein the system of equations includes a plurality of measurements of associated with the mathematical model.

27. The tissue stimulating system of claim 24 wherein the frequency of changes to the amount of power provided to the implantable device from the external device is limited.

28. The tissue stimulating system of claim 24 wherein the size of changes made to the amount of power provided to the implantable device from the external device is limited.

29. The tissue stimulating system of claim 24 wherein the implantable part comprises an Implantable Cochlear Stimulator (ICS), and the external part comprises a Wearable Processor (WP).

30. The tissue stimulating system of claim 24 wherein the implantable part comprises an Implantable Cochlear Stimulator (ICS), and the external part comprises a Behind-The-Ear (BTE) processor.

31. A method for conserving power within a tissue stimulating system, the system comprising an external device and an implantable device, wherein the external device includes a power source for providing operating power for the system, and wherein the external device further includes means for transmitting power to the implantable device, wherein the implantable device includes electrodes for stimulating tissue with electrical power derived from the power transmitted to the implantable device from the external device, the method comprising:

estimating the power requirements of the implantable device, wherein the estimating is performed within the external device, and wherein the estimating does not require feed-back of data from the implantable device; and adjusting the amount of power transmitted to the implantable device so that the amount of power transmitted to the implantable device corresponds to the estimate of the power requirements of the implantable device.

32. The method of claim 31 wherein the step of estimating the power requirement of the implantable device comprises evaluating a mathematical model using measurements originating in the external device.

33. The method of claim 32 wherein the method further comprises:

obtaining the mathematical model, comprising:
collecting measurements of the dependent variable and the independent variables of the mathematical model; and
solving for coefficients of the mathematical model using a multiple regression algorithm;

implementing the mathematical model within the external device to estimate the power required by the implantable device.

34. The method of claim 33 wherein the step of collecting measurements, comprises;

1) implanting the implantable device;
2) connecting test equipment to the tissue stimulation system;
3) stimulating the tissue stimulation system with speech noise;
4) recording the speech noise level (dBSPL);
5) recording the RF power level;
6) recording $V_{tank}$ (where $V_{tank}$ is the voltage on the tank capacitor within the implantable device);
7) repeating steps 2 through 6 at different speech noise; and
8) repeating steps 2 through 7 at different RF power levels.

* * * * *